United States Patent
Doll et al.

(10) Patent No.: US 11,712,553 B2
(45) Date of Patent: Aug. 1, 2023

(54) PATIENT SAFE SUCTION PRESSURE RELIEF VALVE AND METHOD OF USING THE VALVE

(71) Applicant: Pepper Medical Inc., West Chester, PA (US)

(72) Inventors: Gregory E. Doll, Bethesda, MD (US); John Calebaugh, Whitewater, WI (US)

(73) Assignee: Pepper Medical Inc., West Chester, PA (US)

( * ) Notice: Subject to any disclaimer, the term of this patent is extended or adjusted under 35 U.S.C. 154(b) by 568 days.

(21) Appl. No.: 16/741,785

(22) Filed: Jan. 14, 2020

(65) Prior Publication Data

US 2020/0222683 A1 Jul. 16, 2020

Related U.S. Application Data

(60) Provisional application No. 62/792,528, filed on Jan. 15, 2019.

(51) Int. Cl.
*A61M 39/24* (2006.01)
*A61M 39/12* (2006.01)
*F16K 15/14* (2006.01)

(52) U.S. Cl.
CPC ............ *A61M 39/24* (2013.01); *A61M 39/12* (2013.01); *F16K 15/14* (2013.01); *A61M 2039/242* (2013.01); *A61M 2039/2493* (2013.01)

(58) Field of Classification Search
CPC ...... A61M 2039/229; A61M 2039/242; A61M 2039/2493
See application file for complete search history.

(56) References Cited

U.S. PATENT DOCUMENTS

| 4,758,224 A * | 7/1988 | Siposs .................. A61M 39/24 604/129 |
| 6,142,980 A * | 11/2000 | Schalk .................. A61M 1/367 604/129 |
| 7,004,931 B2 | 2/2006 | Hogendijk |
| 2006/0149189 A1* | 7/2006 | Diamond .............. A61M 5/007 604/246 |
| 2010/0249703 A1* | 9/2010 | Cliff ....................... A61C 17/08 604/119 |
| 2012/0191037 A1* | 7/2012 | Patel ..................... F16K 5/0407 604/246 |

OTHER PUBLICATIONS

Czarnik RE, Stone KS, Everhart CC, Preusser BA. Differential effects of continuous versus intermittent suction on tracheal tissue. Heart Lung. 1991;20:144 51.
Wilson R. Bacteria and airway inflammation in chronic obstructive pulmonary disease: more evidence. Am J Respir Crit Care Med. 2005;172:147-8.

* cited by examiner

*Primary Examiner* — Courtney B Fredrickson
(74) *Attorney, Agent, or Firm* — Jeffrey S. Melcher; Melcher Patent Law PLLC

(57) ABSTRACT

A medical suctioning, pressure relief valve having a housing having a central fluid passage way, a first suction tubing connector configured to connect suction tubing to the central fluid passage way, a second suction tubing connector configured to connect suction tubing to the central fluid passage way, and a one-way internal pressure relief valve configured to allow ambient air into the central passage way when a set negative pressure is reached within the central passage. A method of suctioning a fluid from a patient using the medical suctioning, pressure relief valve.

5 Claims, 8 Drawing Sheets

SECTION M-M

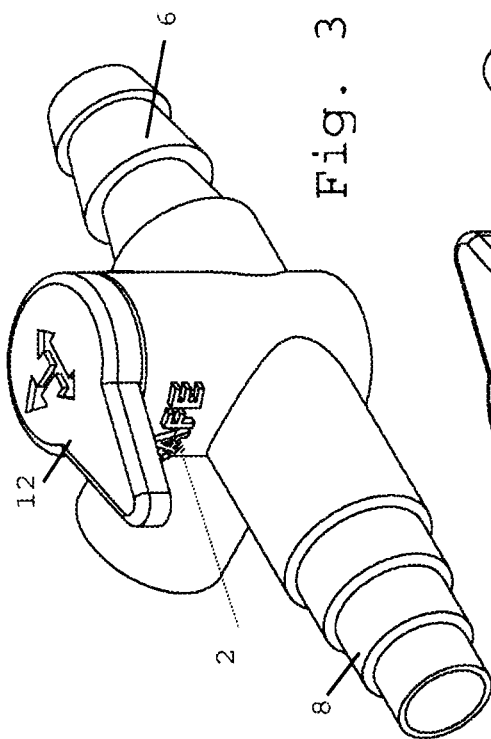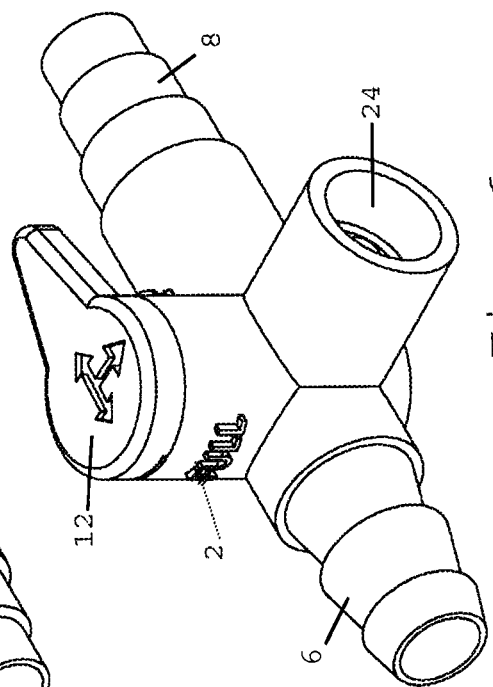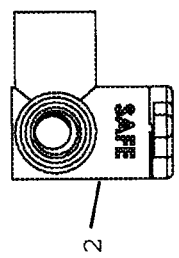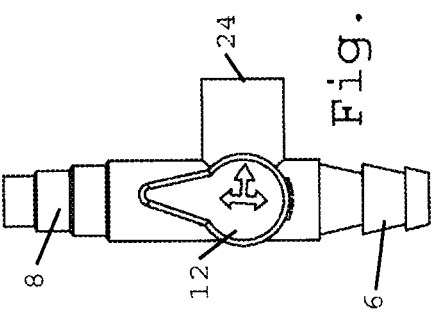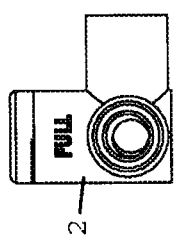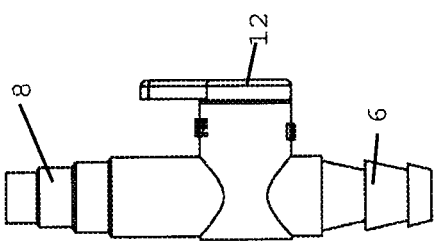

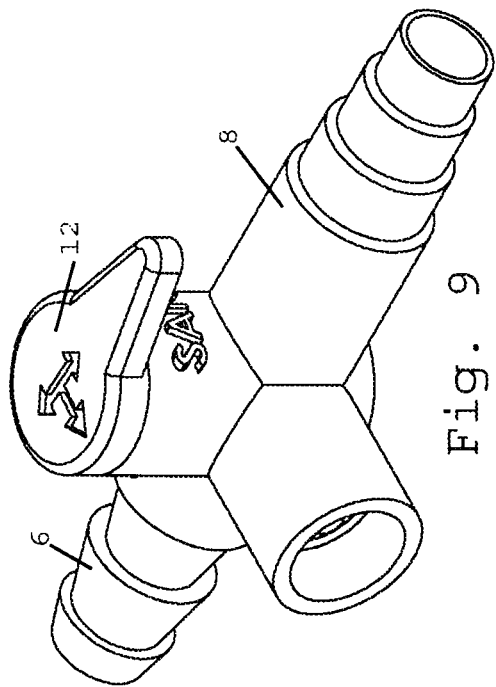
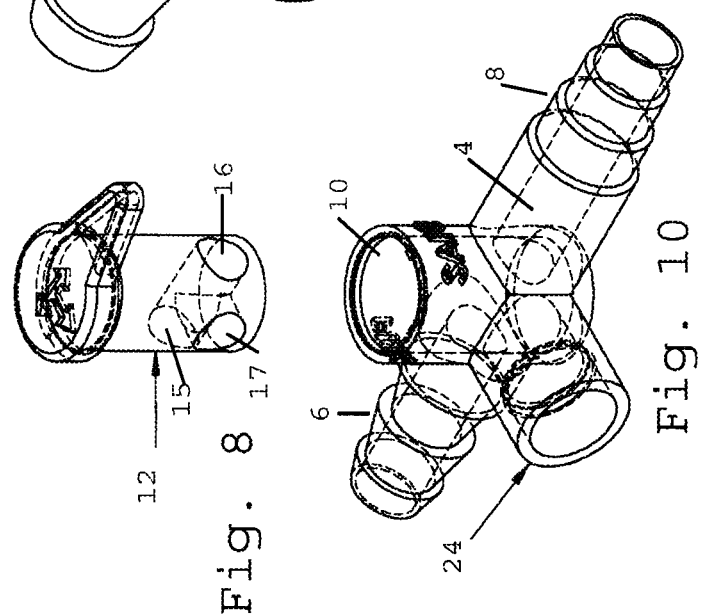
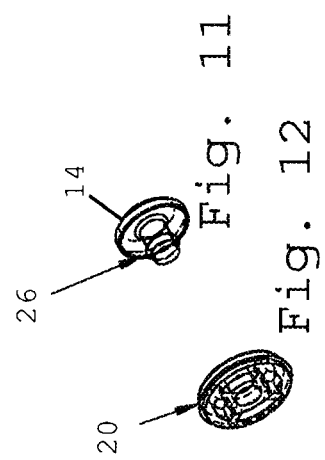

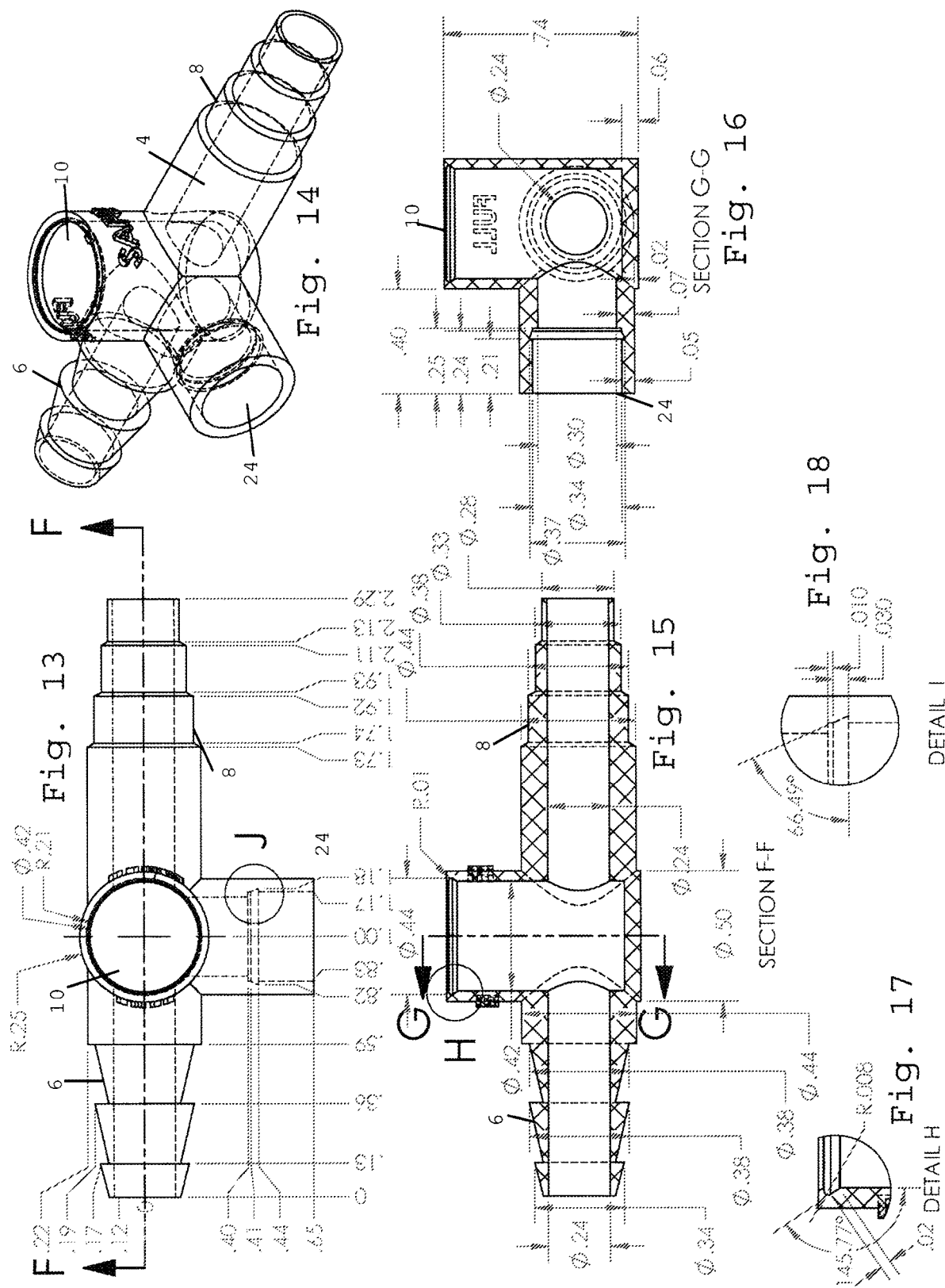

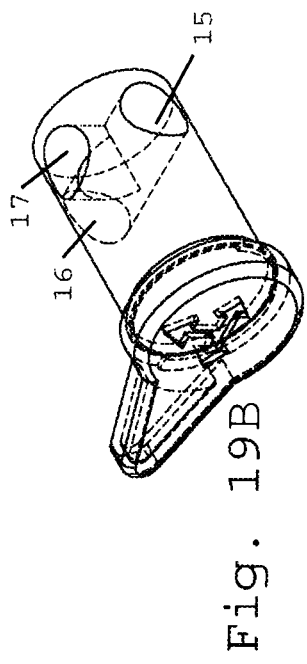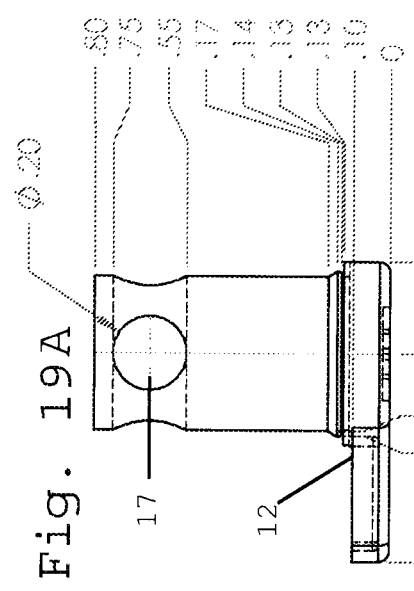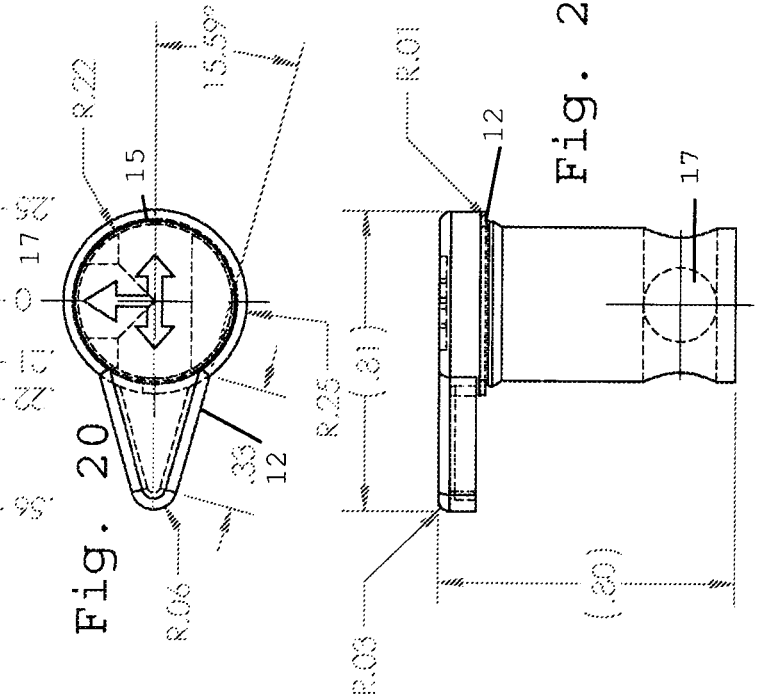

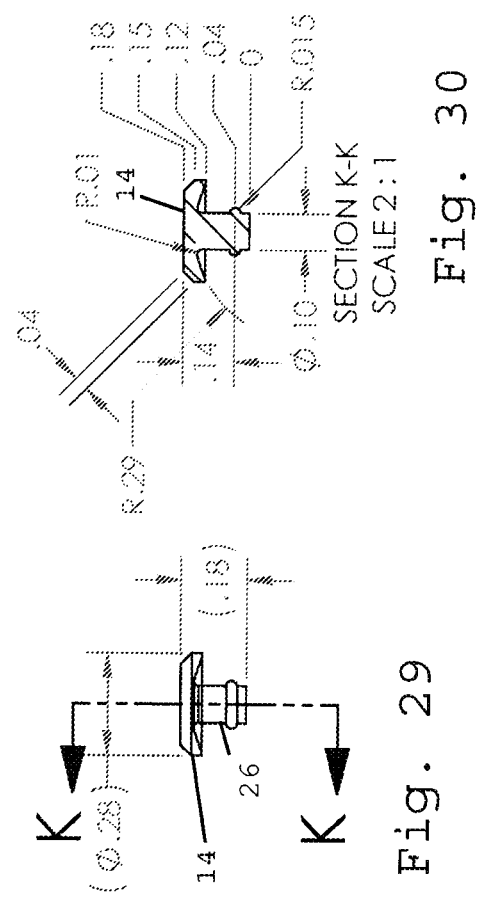

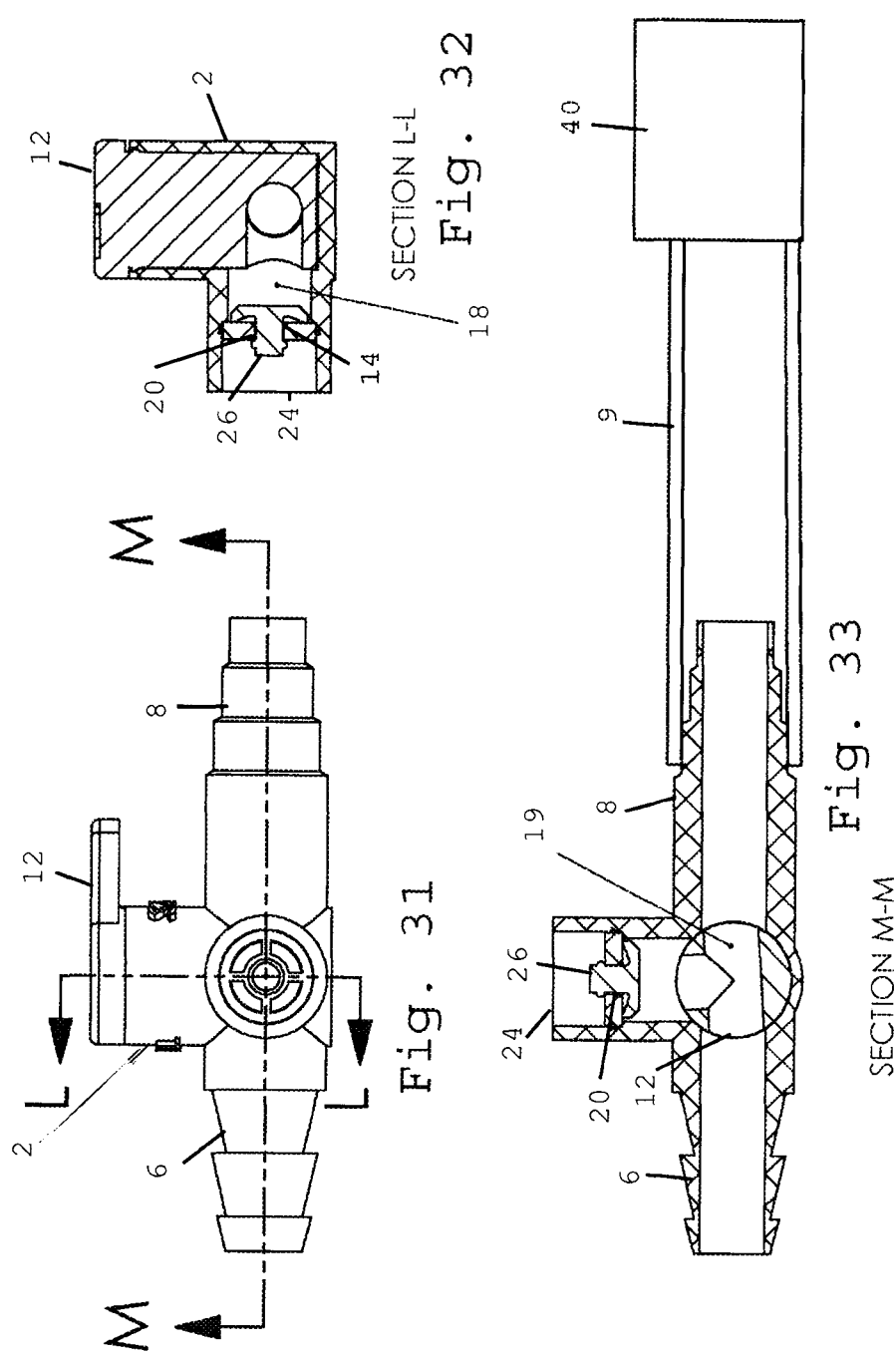

PATIENT SAFE SUCTION PRESSURE RELIEF VALVE AND METHOD OF USING THE VALVE

FIELD OF THE INVENTION

The invention relates to a pressure relief valve providing a maximum safe negative pressure in a suction device and a method of using the pressure relief valve when suctioning a fluid from a patient.

BACKGROUND OF THE INVENTION

Medical suction is an essential part of clinical practice. Since the 1920s, it has been used to empty the stomach, and in the 1950s, airway suction levels were first regulated for safety. Today, medical suction is used for neonates and seniors—and for patients weighing between 500 grams and 500 pounds. Medical suction clears the airway, empties the stomach, decompresses the chest, and keeps the operative field clear. It is essential that clinicians have reliable equipment and supplies that are safe, accurate and easy to use.

The clinical goal is to provide adequate negative pressure to suction the patient airway, stomach, chest and wound without causing damage or compromising the clinical condition and ventilation. Incorrect or high level negative pressure suctioning is associated with complications that include bleeding, infection, hypoxemia, cardiovascular instability, and tracheal mucosal injury.

The current focus on patient safety extends mainly to suction procedures and routines. When suction pressures are too high, mucosal damage occurs, both in the airway (Czamik R E, Stone K S, Everhart C C, Preusser B A. Differential effects of continuous versus intermittent suction on tracheal tissue. *Heart Lung.* 1991; 20:144-51) and in the stomach. If too much negative pressure is applied through a chest tube, lung tissue can be drawn into the eyelets of the thoracic catheter (Duncan C, Erickson R. Pressures associated with chest tube stripping. *Heart Lung.* 1992; 11(2):166-171). Researchers are examining the connection between airway mucosal damage and ventilator-associated pneumonia. In pediatrics, airway suction catheters are inserted to a premeasured length that avoids letting the suction catheter come in contact with the tracheal mucosa distal to the endotracheal tube (Altimier L. Editorial [Evidence-based neonatal respiratory management policy]. *Newborn and Infant Nursing Reviews.* 2006; 6:43-51). Mucosal damage can also be mitigated with appropriate suction techniques, and every effort should be made to reduce this insult to the immune system of patients who are already compromised. Damaged airway mucosa releases nutrients that support bacterial growth (Wilson R. Bacteria and airway inflammation in chronic obstructive pulmonary disease: more evidence. *Am J Respir Crit Care Med.* 2005; 172:147-8), and *Pseudomonas aeruginosa* and other organisms are drawn to damaged epithelium (Dowling R B, Johnson M, Cole P J, Wilson R. Effect of fluticasone propionate and salmeterol on *Pseudomonas aeruginosa* infection of the respiratory mucosa in vitro. *Eur Respir J.* 1999; 14:363-9; Rutman A, Dowling R, Wills P, Feldman C, Cole P J, Wilson R. Effect of dirithromycin on *Haemophilus influenzae* infection on the respiratory mucosa. *Antimicrob Agents Chemother.* 1998; 42:772-8). Mucosal damage in the stomach can result in bleeding and anemia as well as formation of scar tissue.

Additionally, the use of extreme airway suctioning and negative pressure can have substantial impact on ventilator dependent patients and their ventilatory support. This extreme negative pressure can lead to conditions such as 'atelectasis', the reduction in alveoli and lung volume, hypoxemia, and cardiac dysrhythmia. Hypoxia—particularly in significantly debilitated or compromised patient, may lead to tachycardia, arrhythmias and even cardiac arrest. For this reason, the patient must be oxygenated with AMBU or 100% per ventilator before, during, and following the procedure. Dysrhythmias—Serious cardiac dysrhythmias may be caused by hypoxia or vagal stimulation. Increase in intracranial pressure—A prolonged cough maneuver is capable of causing significant increase in intracranial pressure and deleterious effects. Hypotension—This may occur due to bradycardia resulting from vagal stimulation or prolonged cough. Lung collapse—Occluding the tracheal tube with large catheter then suctioning can result in removal of sufficient air to cause collapse of respiratory units. Mucosal damage—The airway mucosa can be damaged by abrasion with the catheter and suctioning.

In summary, improperly set vacuum regulators can expose patients to vacuum pressures up to 15 times higher than recommended pressures for nasogastric or endotracheal suction procedures. Higher than recommended pressures can cause suction-induced lung derecruitment and tear the delicate mucosal tissue in the stomach or trachea, leading to bleeding and potential infection. Research indicates that the prevention of suction-induced lung derecruitment is more clinically relevant than reversal of Acute Lung Injury or Acute Respiratory Distress Syndrome (ARDS). Many clinicians, however, do not fully understand how they can help to prevent these complications through the proper use of vacuum regulators.

Physics of suctioning: Flow rate is the term used to describe how fast air, fluid, or secretions are removed from the patient. Ideally, clinicians need the best flow rate out of a vacuum system at the lowest negative pressure. Three main factors affect the flow rate of a suction system:

The amount of negative pressure (vacuum)
 The resistance of the suction system
 The viscosity of the matter being removed The negative pressure used establishes the pressure gradient that will move air, fluid, or secretions. Material will move from an area of higher pressure in the patient to an area of lower pressure in the suction apparatus. The resistance of the system is determined primarily by the most narrow part of the system—typically, a tubing connector—but the length of tubing in the system can increase resistance as well. Watery fluids such as blood will move through the suction system much more quickly than will thick substances such as sputum and mucus. At one time, it was thought that instilling normal saline into an artificial airway would thin secretions, enhancing the flow of secretions out of the airway, but research shows that no thinning occurs and that patients' oxygenation drops with saline installation. Typically, the accepted safe maximum negative suctioning pressure are:

Adults −100 to −120 mmHg
 Pediatrics −80 to −100 mmHg
 Infants −60 to −80 mmHg
 Egan's Fundamentals of Respiratory Care. Wilkins & Stoller. 9th Edition, page 695. Best Practice: Occlude opening to Set correct pressure for Safety (Occlude to Set).

Wall Vacuum regulators are ever-present in the hospital setting. Clinicians use them daily and may not be as attentive to this equipment given the demands of monitors and devices alarming and competing for the clinician's attention and time.

Few clinicians learn the finer safety points of setting up medical suction systems such as the occlude to set technique. Many nursing fundamentals don't specify critical elements except to tell the nurse to follow manufacturers' instructions. Many clinicians do not learn or implement the critical, universal "occlude to set" step recommended by all North American manufacturers of vacuum regulators. Unregulated Wall negative pressures can be as high as 625 mmHg.

While a number of organizations have published guidelines, ultimately the clinician must determine the maximum allowable level of negative pressure that can be applied to the patient and set the pressure appropriately. This is determined by a number of factors: where the suction pressure is applied (airway, stomach, oropharynx, pleural space, operative field), the age and size of the patient, the susceptibility for mucosal or other tissue damage, and the risks associated with removing air during the suction procedure.

Once the maximum negative pressure level has been determined, the vacuum regulator must be adjusted so that the maximum pressure is locked in; that is, the regulator must be set correctly so it will not permit a higher pressure to be transmitted to the patient, potentially damaging tissue and or causing ventilator distress.

With traditional technology, the clinician must actively occlude the system by either pinching the suction tubing closed, or occluding the nipple adaptor (where the tubing is attached) with a finger. Once the system is occluded, the pressure regulator is set to the maximum desired pressure; then the occlusion is released. If the system is not occluded during setup, the maximum pressure is then unregulated and can spike to harmful levels (see FIGS. 1, 2).

Suctioning is a dynamic process. As catheters are used to remove substances from the body, the degree of open flow continually changes based on the fill of the catheter and the viscosity of the substance being removed. Under these dynamic conditions, the regulator continually compensates by adjusting flow rate within the device and the tubing to maintain the desired negative pressure. Periodically, mucus plugs or particulate matter will occlude the patient tube. If the system was not occluded to establish the maximum safe pressure at setup, pressure will spike to clear the occlusion, and once the occlusion passes, the patient will be subjected to potentially dangerous, unregulated vacuum pressures again. (see FIG. 1).

Current Suction System Setup Supplies—
Wall negative pressure outlet
Vacuum regulator
12-inch connecting tube
1500 cc (empty) collection bottle
6-foot standard connecting tubing 14 Fr. Suction catheter FIG. 1 illustrates results of a bench test of two suction systems. The desired maximum level of suction is 100 mm Hg (A). One system was set at 100 mm Hg with the system open to flow (red line); the other was set by occluding the system to set 100 mm Hg (green line). During open flow, the "occlude to set" system will have a lower pressure than the desired maximum pressure because there are no occlusions in the system (B). Once suctioning begins, a dynamic flow condition occurs with varying levels of obstruction, and pressure rises in both systems. The point of maximum suction is key. In the "occlude to set" system, the pressure never rises above the desired maximum pressure of 100 mm Hg. In the other system, pressure in this bench test spiked to 125 mm Hg of unregulated suction. Without "occlude to set," the pressure can rise to 25% higher than the desired maximum level or more, exposing the patient to a safety hazard when regulated suction is needed.

Higher negative pressure is a particular hazard for patients with friable mucosa in the airway or stomach, making it more susceptible to traumatic tears. It is also a hazard for infants who have small lung volumes. When all other variables are stable, a 25% increase in negative pressure will increase the amount of air pulled through the system by 25%. That increase could result in a significant loss of lung volume in intubated neonates and infants (Morrow B R, Futter M J, Argent A C. Endotracheal suctioning: from principles to practice. *Neonatal and Pediatric Intensive Care.* 2004; 30:1167-74).

There is a need for a safer device and method for providing medical suctioning to a patient.

SUMMARY OF THE INVENTION

An objective of the invention is to provide a safer method and device for providing medical suctioning to a patient. The one-way pressure relief valve (PRV) helps to ensure that all clinicians, regardless of training or level of competency, do not increase the risks and damage inherent in patient suctioning.

The present invention provides a safety device that removes clinician variables as much as possible by providing added safety passively, while the clinician carries out the suctioning procedure. Traditionally, the optimal safety of regulated vacuum pressure has depended on the clinician's advanced action to occlude the system to set maximum pressure. The present device, 'Safe Suction' PRV, is a passive solution to adjust the pressure level with an easy to apply, one-way pressure relief valve that will open if the internal negative pressure raises above the predetermined valve opening pressure. Examples of the predetermined valve release pressures can be 150 mmHg for Adults, 130 mmHg for Pediatrics and 100 mmHg for neonates. These PRV valve opening pressure can be altered and changed as clinical conditions deem necessary, size of patient or other parameters dictate.

The use of a PRV in the present device provides an effective, passive safety system that removes the clinician variable and protects the patient from unintended, unregulated pressure spikes during suction procedures. The PRV device assures the clinician that the patient will not be subjected to negative pressure higher than clinically acceptable.

Another key safety aspect of the PRV is the ability to quickly adjust to full vacuum mode when emergency strikes and rapid evacuation is essential such as if the patient aspirates on vomit, sputum, or other foreign bodies.

An 'override' system or stopcock provides the clinician with the ability to control vacuum levels more precisely in these situations. This override or full vacuum feature may be needed in emergency conditions to enhance responsiveness and save time. The PRV safe suction can implement such an override or stopcock system that the clinician can quickly and efficiently activate higher negative pressures if needed in an emergency by removing the PRV from the suction flow path.

The Safe Suction PRV comprises a one-way valve and override technology that provides passive safety protection, enhanced control of vacuum pressures, rapid response, and ease of use—all of which contribute to a culture of safety around the patient.

BRIEF DESCRIPTION OF THE DRAWINGS

FIG. 2 illustrates a side view of the medical suctioning, pressure relief valve.

FIG. 3 illustrates a perspective view of the medical suctioning, pressure relief valve.

FIG. 4 illustrates a side view of the medical suctioning, pressure relief valve.

FIG. 5 illustrates a top view of the medical suctioning, pressure relief valve.

FIG. 6 illustrates a perspective view of the medical suctioning, pressure relief valve.

FIG. 7 illustrates a side view of the medical suctioning, pressure relief valve.

FIG. 8 illustrates a perspective view of the override valve.

FIG. 9 illustrates 3 illustrates a perspective view of the medical suctioning, pressure relief valve.

FIG. 10 illustrates a perspective view of the housing.

FIG. 11 illustrates a perspective view of the one-way internal pressure relief valve.

FIG. 12 illustrates a perspective view of the one-way internal pressure relief valve connector.

FIG. 13 illustrates a top view of the housing.

FIG. 14 illustrates a perspective view of the housing.

FIG. 15 illustrates a side view of the housing.

FIG. 16 illustrates a side view of the housing.

FIG. 17 illustrates a partial view of the housing.

FIG. 18 illustrates a partial view of the housing.

FIG. 19A illustrates a side view of the override valve.

FIG. 19B illustrates a perspective view of the override valve.

FIG. 20 illustrates a top view of the override valve.

FIG. 21 illustrates a side view of the override valve.

FIG. 22 illustrates a side view of the override valve.

FIG. 27 illustrates a top view of the one-way internal pressure relief valve.

FIG. 28 illustrates a perspective view of the one-way internal pressure relief valve.

FIG. 28 illustrates a side view of the one-way internal pressure relief valve.

FIG. 29 illustrates a cut-away view of the one-way internal pressure relief valve.

FIG. 31 illustrates a side view of the one-way internal pressure relief valve mounted in the medical suctioning, pressure relief valve.

FIG. 32 illustrates a cut-away view of the one-way internal pressure relief valve mounted in the medical suctioning, pressure relief valve.

FIG. 33 illustrates the medical suctioning, pressure relief valve connected to a vacuum source.

DETAILED DESCRIPTION OF THE INVENTION

Figure 1:
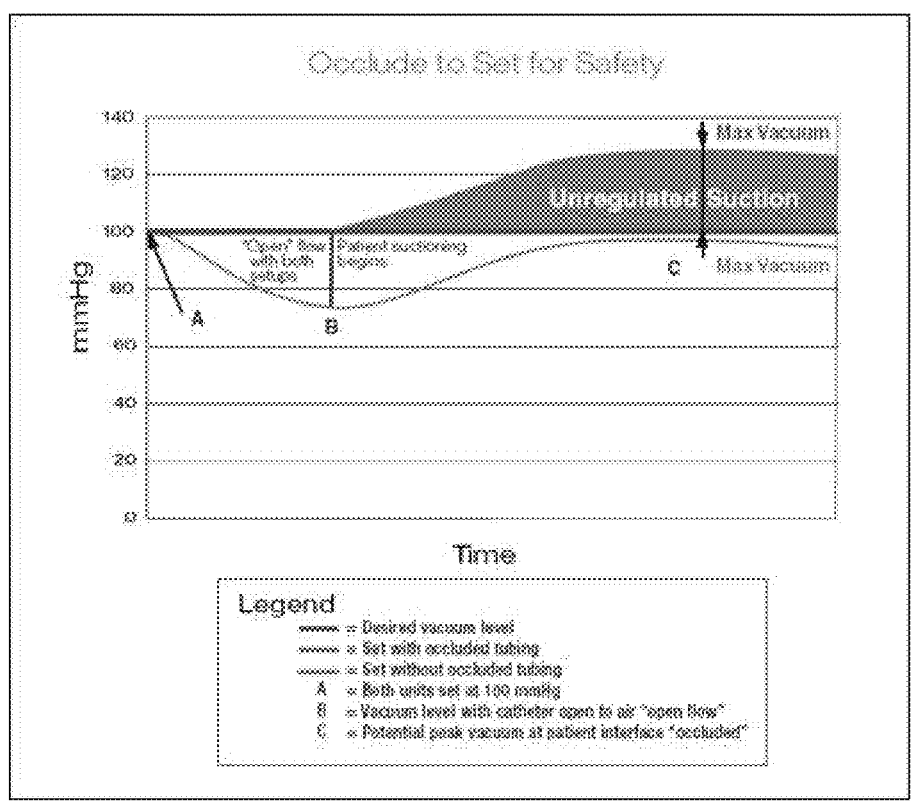
FIG. 1 illustrates the graphical results of a bench test of two suction systems.
Figure 23:
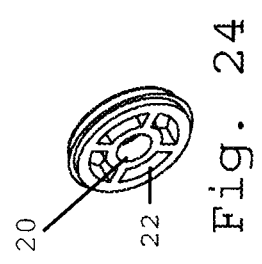
FIG. 23 illustrates a side view of the one-way valve connector.
Figure 24:
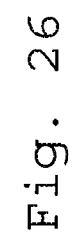
FIG. 24 illustrates a perspective view of the one-way valve connector.
Figure 25:
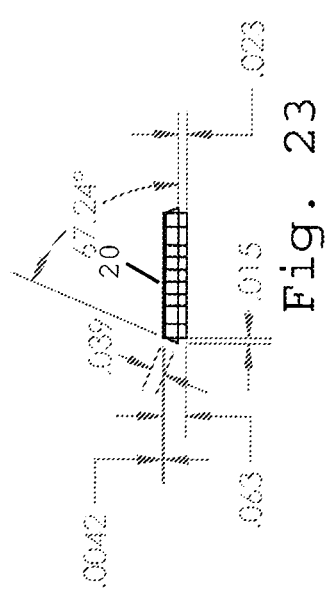
FIG. 25 illustrates a top view of the one-way valve connector.
Figure 26:
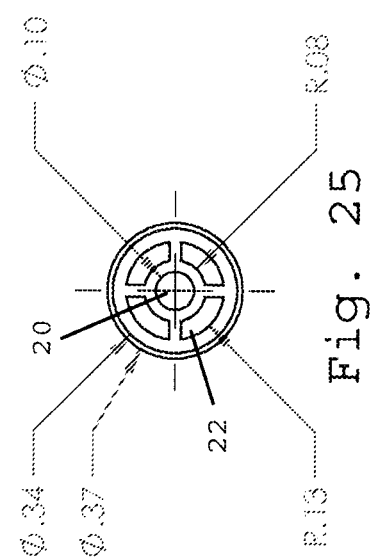
FIG. 26 illustrates a side view of the one-way valve connector.

The medical suctioning, pressure relief valve will be explained with reference to the attached non-limiting FIGS. 2-33. The medical suctioning, pressure relief valve includes a rigid housing 2 defining a central fluid passage way 4. The housing 2 has a first suction tubing connector 6 and a second suction tubing connector 8 so that when suction tubing 9 is connected to the first and second suction tubing connectors 6, 8 fluids can pass through the suction tubing 9, the first suction tubing connector 6, the central passage way 4, and through the second suction tubing connector 8. The housing 2 defines a valve chamber 10 and an atmosphere outlet 24, both of which can be connected to the central passage way 4. A one-way internal pressure relief valve (PRV) 14 can be present in the outlet 24 to limit a maximum level of suction negative pressure in the central passage way.

The first and second suction tubing connectors 6 and 8 can be any desired type of connector configured for connecting to suction tubing 9 to provide a fluid connection. An example of such a connector is tapered and designed to accept suction tubing 9 push-fitted on to each end of housing 2, as shown in the figures.

The central fluid transfer passage way 4 can have generally parallel inner side walls to allow for the passage way of negative pressure suction of fluids when attached to suction tubing 9 and negative pressure. These fluids are suctioned and cleared from the patient by a vacuum source 40 connected to the suction tubing 9.

The housing 2 defines a valve chamber 10 having an override valve 12. The override valve 12 has openings 15 and 16 to allow flow through the valve passage 19 in the override valve 12 and central passage way 4 when in both a closed and open position. The override valve 12 also has an opening 17 connected to the valve passage 19. When the override valve 12 is in a closed position suction flow can only pass through the openings 15 and 16, valve passage 19, and the central passage way 4, bypassing the outlet 24 and PRV 14. When the override valve 12 is in the open position air can enter through the PRV 14 and outlet 24 into the valve passage 19 and central passageway 4 when the suction negative pressure in the central passage way is greater than an amount set by the PRV 14. Thus, the override valve 12 is configured to allow fluid to pass through a fluid openings 15, 16 and through the central passage way 4 when in an open position with the maximum suction level being controlled by the PRV 14. When in a closed position, the override valve 12 is configured to remove the PRV 14 from the suction flow path to provide maximum suction negative pressure in the central passage way 14. For example, the override valve 12 can have a stopcock assembly comprising an open in-line handle position and a closed perpendicular position upon ¼ turn of the handle. The PRV 14 can be removed from the suction flow path in an emergency by closing the valve 12, which can include patient aspiration of vomit, sputum, food, etc. where the clinician deems it necessary to increase negative suction pressure greater than the PRV 14 suction limits will allow.

The outlet 24 can contain the one-way internal pressure relief valve 14 (PRV) and a valve connector 20, which is configured to allow ambient air into the central passage way 4 when a set negative pressure is reached within the central passage way 4. The outlet 24 can have a valve seating that will accept the valve connector 20 and the pressure relief valve 14 in the form of a push-in, self-seating umbrella valve.

The seated one-way valve 14 is designed to open or crack when the internal housing (passage way 4) and tubing system negative pressure exceeds the predetermined valve set negative pressure limits. Examples of these limits open the valve at approximately 150 mmHg for adult size, 125 mmHg for Pediatric size and 100 mmHg for infant size. The housing 2 or housing components may be color coded or otherwise noted to represent the sizing accordingly. For example, the umbrella valve 14 can be modeled of 50 shore, 40 shore and 30 shore durometer respectively. While an umbrella valve is shown, the invention is not limited to any type of valve. Examples of other suitable valves include flapper, ball, and duckbill.

The opening 24 can have a tapered internal wall 18 that can releasably hold the valve 14 against the relief valve opening 22 to seal the relief valve opening 22. The valve 14 also can have a connection portion 26 that is pressed through the relief valve opening in the connector 20. The connection portion 26 can bias the valve 14 against the relief valve opening 22 to seal the relief valve opening 22 by stretching the connection portion when the valve 14 is formed from a flexible, stretchable material such as rubber.

A primary object of the present invention to provide a housing with pressure relief valve and stopcock flow control which can directly connect to a wide variety of different size suction tubing on both housing ends.

Another object of the present invention is to provide a one-way internal pressure relief valve (PRV) 14 that can open or crack upon predetermined set negative pressure. This one-way PRV is easy to assembly and can be adapted to provide a range of opening pressure for various patient sizes and weights.

Another object of the present invention is to provide a one-way internal pressure relief valve (PRV) 14 which can be easily removed from the housing 2 and replaced and inexpensively manufactured.

Another object of the present invention is to provide a one-way internal pressure relief valve (PRV) 14 and housing with corresponding controllable stopcock to close off PRV 14 in case of patient emergency or clinician preference. This could include patient aspiration of vomit, sputum, food, etc. where the clinician deems it necessary to increase negative suction pressure greater that the valve opening limits will allow.

The one-way internal pressure relief valve 14 can be formed of any suitable material. Suitable materials for one-way valves are well known in the medical industry. Examples are plastics and rubbers.

The rigid parts of the medical suctioning, pressure relief valve, such as the housing 2, connectors 6, 8, and override valve 12 can be formed of any suitable material. Suitable materials for one-way valves are well known in the medical industry. Examples are metals, alloys, plastics and composites.

Other advantages, objects, and features of the present invention will become readily apparent from the following detailed description of the invention, from the claims, and from the accompanying drawings.

TERMS 2 medical suctioning, pressure relief valve housing
4 central fluid passage way
6 first suction tubing connector
8 second suction tubing connector
9 suction tubing
10 a valve chamber in the housing 2
12 override valve in the valve cavity
14 one-way internal pressure relief valve
15, 16 fluid openings in override valve 12
17 air inlet of override valve 12
18 tapered inner wall
19 passage in override valve 12
20 relieve valve connector
22 relief valve opening
24 atmosphere opening in housing 2
26 connection portion of the valve 14.
40 vacuum source

REFERENCES

Patricia Carroll, RN, BC, CEN, RRT, MS, is the quality management coordinator at Franciscan Home Care and Hospice Care in Meriden, Conn.
1. Czamik R E, Stone K S, Everhart C C, Preusser B A. Differential effects of continuous versus intermittent suction on tracheal tissue. *Heart Lung.* 1991; 20:144-51.
2. Duncan C, Erickson R. Pressures associated with chest tube stripping. *Heart Lung.* 1992; 11(2):166-171.
3. Altimier L. Editorial [Evidence-based neonatal respiratory management policy]. *Newborn and Infant Nursing Reviews.* 2006; 6:43-51.
4. Wilson R. Bacteria and airway inflammation in chronic obstructive pulmonary disease: more evidence. *Am J Respir Crit Care Med.* 2005; 172:147-8.
5. Dowling R B, Johnson M, Cole P J, Wilson R. Effect of fluticasone propionate and salmeterol on *Pseudomonas aeruginosa* infection of the respiratory mucosa in vitro. *Eur Respir J.* 1999; 14:363-9.
6. Rutman A, Dowling R, Wills P, Feldman C, Cole P J, Wilson R. Effect of dirithromycin on *Haemophilus influenzae* infection on the respiratory mucosa. *Antimicrob Agents Chemother.* 1998; 42:772-8.
7. Ackerman M H, Ecklund M M, Abu-Jumah. A review of normal saline installation: implications for practice. *Dimens Crit Care Nurs.* 1996; 15:1531-8.
8. Raymond S J. Normal saline instillation before suctioning: helpful or harmful? A review of the literature. *Am J Crit Care.* 1995; 4:267-71.
9. Vandenberg J T, Rudman N T, Burke T F, Ramos D E. Large-diameter suction tubing significantly improves evacuation time of simulated vomitus. *Am J Emerg Med.* 1998; 16:242-4.
10. Vandenberg J T, Lutz R H, Vinson D R. Large-diameter suction system reduces oropharyngeal evacuation time. *J Emerg Med.* 1999; 17:941-4.
11. Vandenberg J T, Vinson D R. The inadequacies of contemporary oropharyngeal suction. *Am J Emerg Med.* 1999; 17:611-3.
12. Wilkinson J M, VanLeuven K. Fundamentals of Nursing: Thinking and Doing. Vol 2. Philadelphia: *FA Davis Company;* 2007.
13. Morrow B R, Futter M J, Argent A C. Endotracheal suctioning: from principles to practice. *Neonatal and Pediatric Intensive Care.* 2004; 30:1167-74.

The invention claimed is:
1. An assembly comprising:
  a housing having a central fluid passage way and defining an opening;
  a first suction tubing connector configured to connect suction tubing to the central fluid passage way;
  a second suction tubing connector configured to connect suction tubing to the central fluid passage way;
  a one-way internal pressure relief valve configured to allow ambient air into the central fluid passage way when a set negative pressure is reached within the central fluid passage way, wherein the one-way internal pressure relief valve comprising a valve connector removably mounted within the opening;
  an override valve configured to allow an operator to override the one-way internal pressure relief valve and provide maximum suction through the central fluid passage way.

2. The assembly according to claim 1, wherein the override valve being removably disposed in a valve chamber.

3. A method of medical suctioning a fluid from a patient comprising:
- providing an assembly according to claim 1 connected to a vacuum source by suction tubing; and
- suctioning a fluid from a patient through the assembly wherein the one-way internal pressure relief valve opens to allow ambient air into the central fluid passage way when the set negative pressure is reached within the central fluid passage way.

4. The method according to claim 3, further comprising operating the override valve to override the one-way internal pressure relief valve to provide a negative pressure in the central fluid passage way greater than the set negative pressure of the one-way internal pressure relief valve.

5. The method according to claim 3, further comprising removing the one-way internal pressure relief valve from the assembly and installing a new one-way internal pressure relief valve having a desired opening pressure.

* * * * *